United States Patent
Son et al.

(10) Patent No.: US 11,519,854 B2
(45) Date of Patent: Dec. 6, 2022

(54) DNA ANALYSIS METHOD AND DNA ANALYSIS APPARATUS USING TERAHERTZ WAVE

(71) Applicants: UNIVERSITY OF SEOUL INDUSTRY COOPERATION FOUNDATION, Seoul (KR); SEOUL NATIONAL UNIVERSITY HOSPITAL, Seoul (KR)

(72) Inventors: Joohiuk Son, Seoul (KR); Hwayeong Cheon, Seoul (KR); Heejin Yang, Seoul (KR)

(73) Assignees: UNIVERSITY OF SEOUL INDUSTRY COOPERATION FOUNDATION, Seoul (KR); SEOUL NATIONAL UNIVERSITY HOSPITAL, Seoul (KR)

( * ) Notice: Subject to any disclaimer, the term of this patent is extended or adjusted under 35 U.S.C. 154(b) by 856 days.

(21) Appl. No.: 16/466,041

(22) PCT Filed: Nov. 16, 2017

(86) PCT No.: PCT/KR2017/013031
§ 371 (c)(1),
(2) Date: Jun. 3, 2019

(87) PCT Pub. No.: WO2018/101657
PCT Pub. Date: Jun. 7, 2018

(65) Prior Publication Data
US 2020/0064258 A1    Feb. 27, 2020

(30) Foreign Application Priority Data
Dec. 1, 2016 (KR) .................. 10-2016-0163025

(51) Int. Cl.
*G01N 21/3581* (2014.01)
*C12Q 1/6809* (2018.01)
(Continued)

(52) U.S. Cl.
CPC ....... *G01N 21/3581* (2013.01); *C12Q 1/6809* (2013.01); *G01N 33/487* (2013.01); *G01N 2021/3196* (2013.01)

(58) Field of Classification Search
CPC ............ G01N 21/3581; G01N 33/487; G01N 2021/3196; C12Q 1/6809
See application file for complete search history.

(56) References Cited

U.S. PATENT DOCUMENTS

2007/0073115 A1   3/2007 Hwang
2013/0130237 A1*  5/2013 Ouchi ................... A61B 6/00
                                                       435/6.1

(Continued)

FOREIGN PATENT DOCUMENTS

CA    2842458      6/2014
JP    2005-172775 A  6/2005
(Continued)

*Primary Examiner* — Jamil Ahmed
(74) *Attorney, Agent, or Firm* — Adam Warwick Bell

(57) ABSTRACT

A DNA analysis method and a DNA analyzing device using terahertz wave capable of accurately determining a type of cancer from DNA using terahertz wave are disclosed. The DNA analysis method according to the present invention comprises: (a) irradiating terahertz wave onto methylated DNA; (b) detecting the terahertz wave reflected from the methylated DNA; (c) detecting a peak of a waveform of the terahertz wave detected in the step (b); and (d) determining type of cancer from the peak detected in the step (c).

6 Claims, 8 Drawing Sheets

(51) Int. Cl.
*G01N 21/31* (2006.01)
*G01N 33/487* (2006.01)

(56) References Cited

U.S. PATENT DOCUMENTS

2014/0070102 A1 3/2014 Globus
2016/0305995 A1 10/2016 Kim et al.

FOREIGN PATENT DOCUMENTS

| JP | 2005-334129 A | 12/2005 |
| JP | 2013-127451 A | 6/2013 |
| KR | 10-2007-0034169 A | 3/2007 |
| KR | 10-2016-0124406 A | 10/2016 |

* cited by examiner

<Prior Art>

\<Prior Art\>

DNA ANALYSIS METHOD AND DNA ANALYSIS APPARATUS USING TERAHERTZ WAVE

BACKGROUND OF THE INVENTION

1. Technical Field

The present invention relates to a DNA analysis method and a DNA analyzing device using terahertz wave, and more particularly, to a DNA analysis method and a DNA analyzing device using terahertz wave capable of accurately determining a type of cancer from DNA using terahertz wave.

2. Description of the Related Art

The methylation of DNA is known to be one of the key mechanisms of cancer development. The methylation of DNA, which is a tumor marker, is a phenomenon that occurs early in cancer development and is universally found in almost all cancers and has unique characteristics depending on each organ of the human body.

FIGS. 1A and 1B are diagrams schematically illustrating DNA of normal cells and DNA of cancer cells. FIG. As shown in FIGS. 1A and 1B, the DNA of the cancer cell differs from that of normal cells in that methylation occurs when cancer develops. Therefore, carcinogenesis can be confirmed when the methylation of DNA is measured.

A quantitative method to accurately measure the degree of methylation of DNA is required in order to diagnose a carcinogenesis.

One of the quantitative measurement methods is the bisulfite conversion method and the array method shown in FIG. 2. According to the bisulfite conversion method, uracil is generated in non-methylated DNA by a deamination reaction. The DNA treated by the bisulfite conversion method is subjected to PCR amplification and sequencing to measure the degree of methylation of DNA.

As another quantitative measurement method, there is an ELISA-like method shown in FIG. 3. The ELISA-like method is a method for measuring the degree of methylation of DNA through the process shown in FIG. 3.

The bisulfite conversion method, the array method and the ELISA-like method require complex pretreatment process and markers for measurement. Despite these complex pretreatment processes, the bisulfite conversion method, the array method and ELISA-like methods have relatively low accuracy. Therefore, there is a need for a new method and apparatus for accurately diagnosing type of cancer as well as diagnosis of carcinogenesis.

PRIOR ARTS

Patents

Patent Document 1: U.S. Patent Application Publication No. 2014/0070102

Patent Document 2: U.S. Patent Application Publication No. 2013/0130237

Patent Document 3: Canadian Patent Application Publication No. 2842458

SUMMARY OF THE INVENTION

It is an object of the present invention to provide a DNA analysis method and a DNA analyzing device using terahertz wave capable of accurately determining a type of cancer from DNA using terahertz wave.

According to one aspect of the present invention, there is provided a DNA analysis method, comprising: (a) irradiating terahertz wave onto methylated DNA; (b) detecting the terahertz wave reflected from the methylated DNA; (c) detecting a peak of a waveform of the terahertz wave detected in the step (b); and (d) determining type of cancer from the peak detected in the step (c).

It is preferable that the step (c) comprises: (c-1) fitting the waveform into a sum of a first gaussian function and a second gaussian function; and (c-2) detecting a peak of the first gaussian function and a frequency of the terahertz wave corresponding to the peak of the first gaussian function.

It is preferable that the step (d) comprises: determining the type of cancer from the frequency of the terahertz wave corresponding to the peak of the first gaussian function detected in the step (c-2).

It is preferable that the step (a) comprises: irradiating the terahertz wave onto methylated DNA while varying a frequency of the terahertz wave.

According to another aspect of the present invention, there is provided a DNA analyzing device, comprising: a terahertz wave irradiator irradiating terahertz wave onto methylated DNA; a terahertz wave detector detecting the terahertz wave reflected from the methylated DNA; a peak detector detecting a peak of a waveform of the terahertz wave detected by the terahertz wave detector; and a determination unit determining a type of cancer from the peak detected by the peak detector.

It is preferable that the peak detector comprises: a waveform fitting unit fitting the waveform into a sum of a first gaussian function and a second gaussian function; and a gaussian peak detector detecting a peak of the first gaussian function and a frequency of the terahertz wave corresponding to the peak of the first gaussian function.

It is preferable that the determination unit determining the type of cancer from the frequency of the terahertz wave corresponding to the peak of the first gaussian function detected by the gaussian peak detector.

It is preferable that the terahertz wave irradiator irradiates the terahertz wave onto methylated DNA while varying a frequency of the terahertz wave.

DETAILED DESCRIPTION OF EMBODIMENTS

Hereinafter, preferred embodiments of the present invention will be described in detail with reference to the accompanying drawings.

Figure 1A:
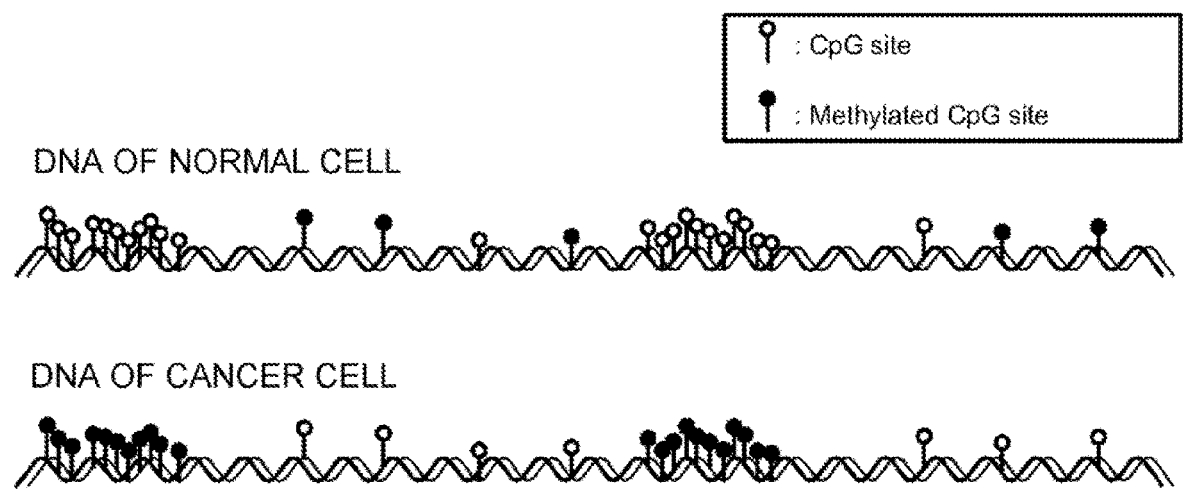
FIGS. 1A and 1B are diagrams schematically illustrating DNA of normal cells and DNA of cancer cells.
Figure 1B:
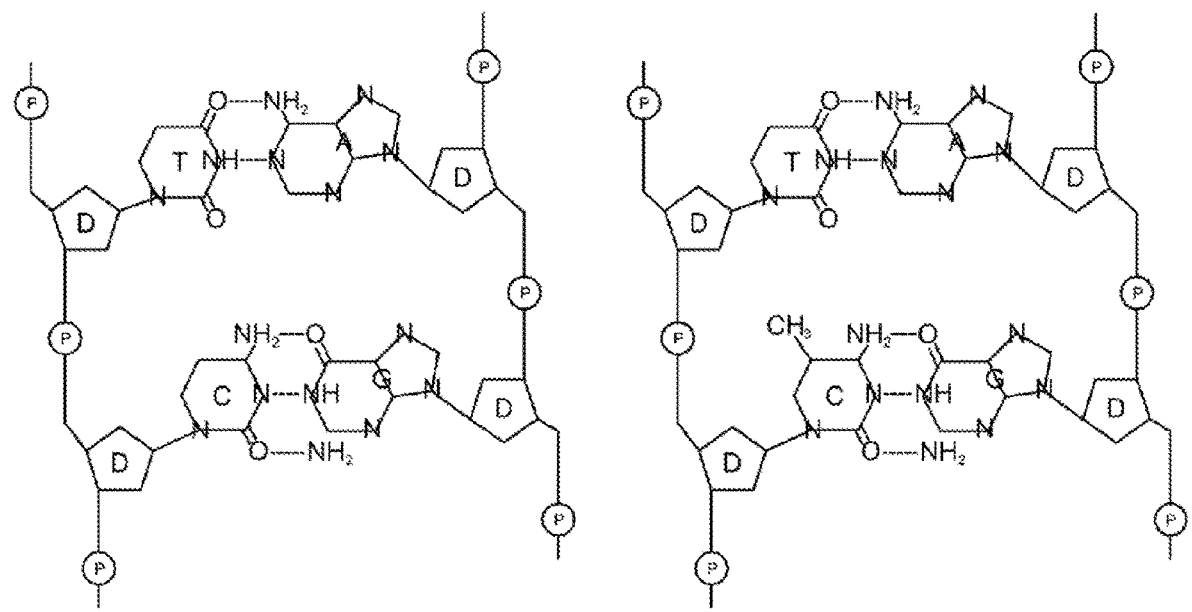
Figure 2:
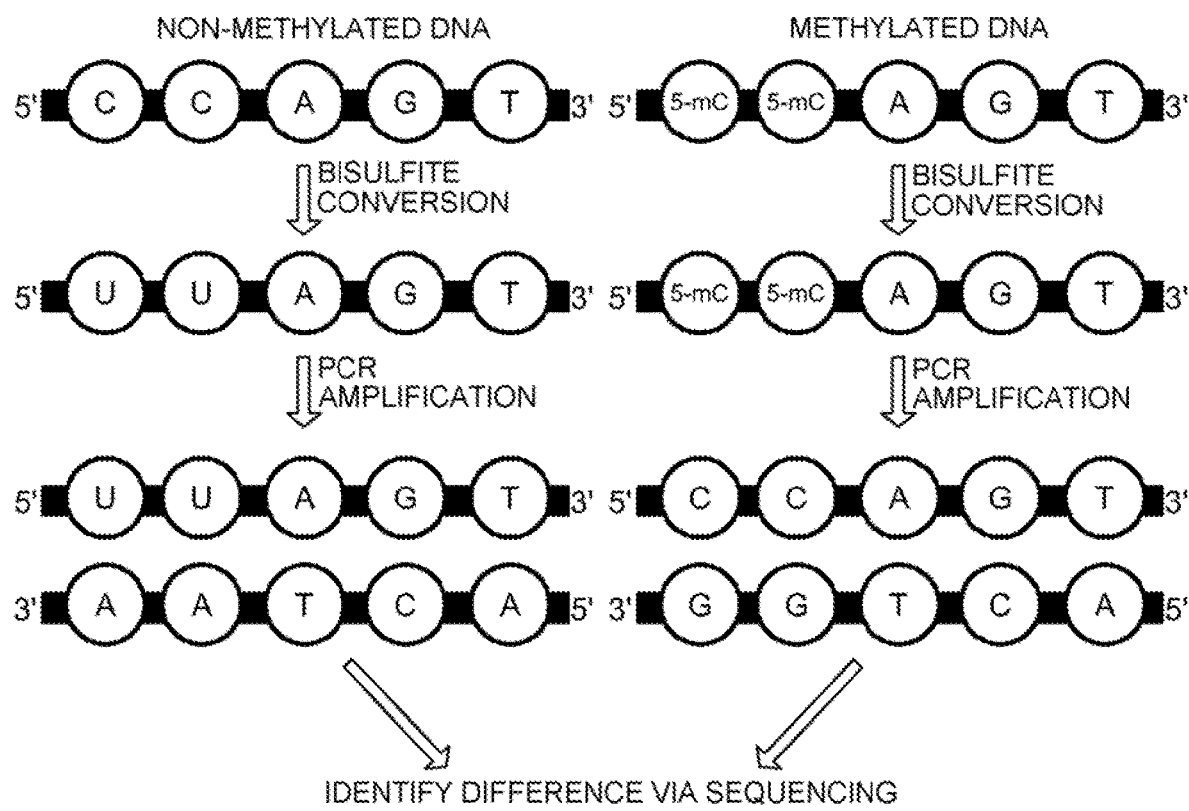
FIG. 2 illustrates a bisulfite conversion method and an array method according to the prior art.
Figure 3:
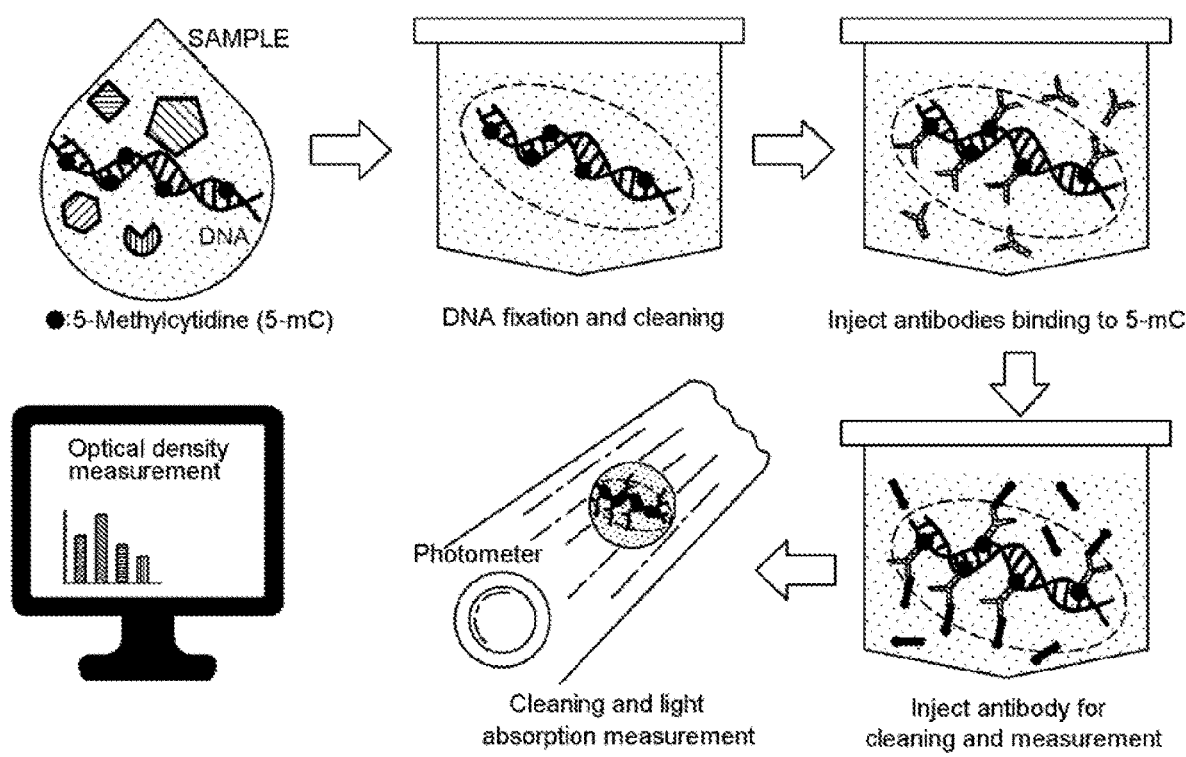
FIG. 3 illustrates ELISA-like method according to the prior art.
Figure 4:
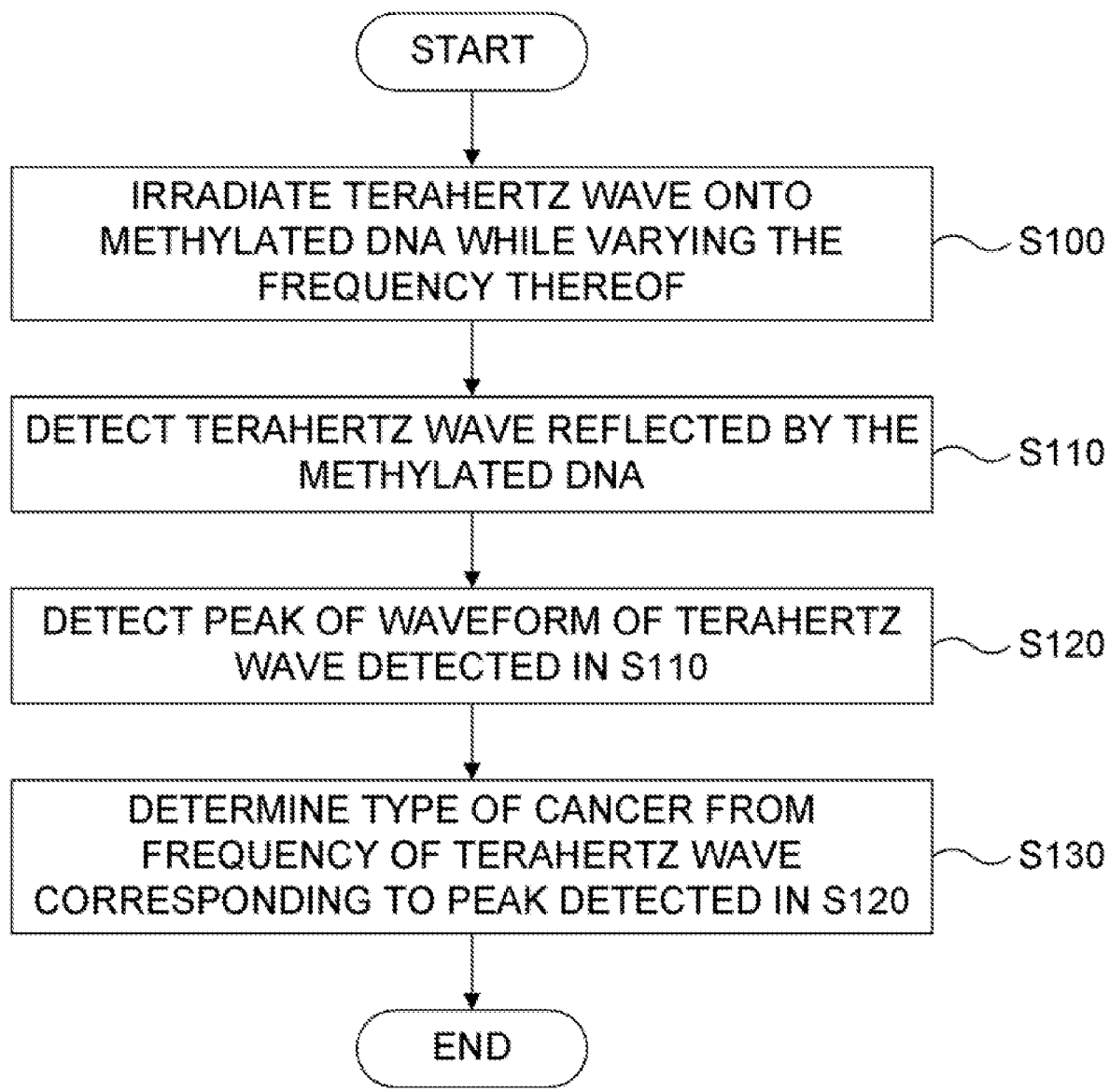
FIG. 4 is a flowchart illustrating a DNA analysis method using terahertz wave according to the present invention.

FIG. 4 is a flowchart illustrating a DNA analysis method using terahertz wave according to the present invention. Referring to FIG. 4, terahertz wave is irradiated onto methylated DNA (S100). It is preferable to irradiate the methylated DNA with the terahertz wave while varying the frequency of the terahertz wave irradiated onto the methylated DNA. For example, the frequency of the terahertz wave may be varied from 0.4 THz to 2.5 THz while the terahertz wave is irradiated onto methylated DNA.

Thereafter, the terahertz wave reflected by the methylated DNA is detected (S110). When methylated DNA is irradiated with terahertz wave, one portion of the terahertz wave is transmitted through the methylated DNA and another portion the terahertz wave is reflected. The reflected terahertz wave contains unique information about the methylated DNA. For example, the terahertz wave reflected from DNA of skin cancer cells differs from the terahertz wave reflected from the DNA of prostate cancer cells. This will be described in detail later.

Thereafter, the peak of the waveform of the terahertz wave detected in step S110 is detected (S120).

Figure 5A:
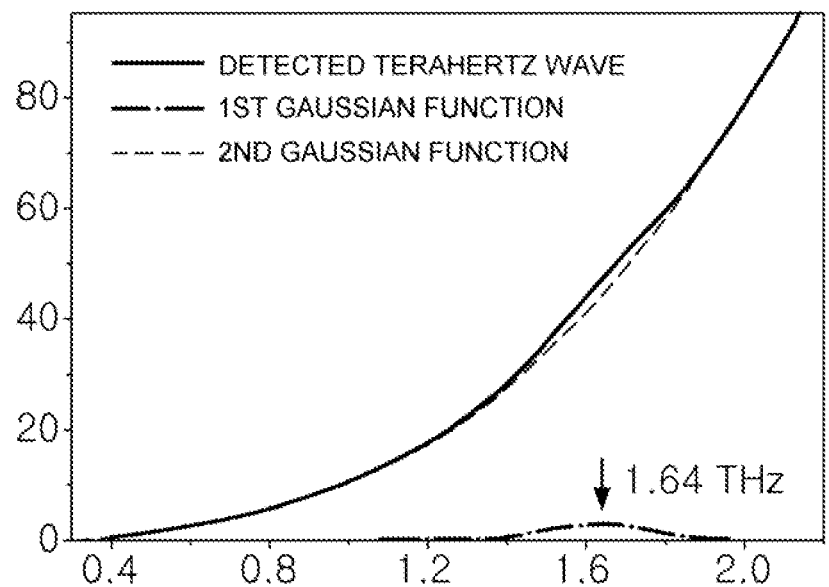
FIGS. 5A through 5D are graphs showing waveforms of the detected terahertz wave according to the present invention.
Figure 5B:
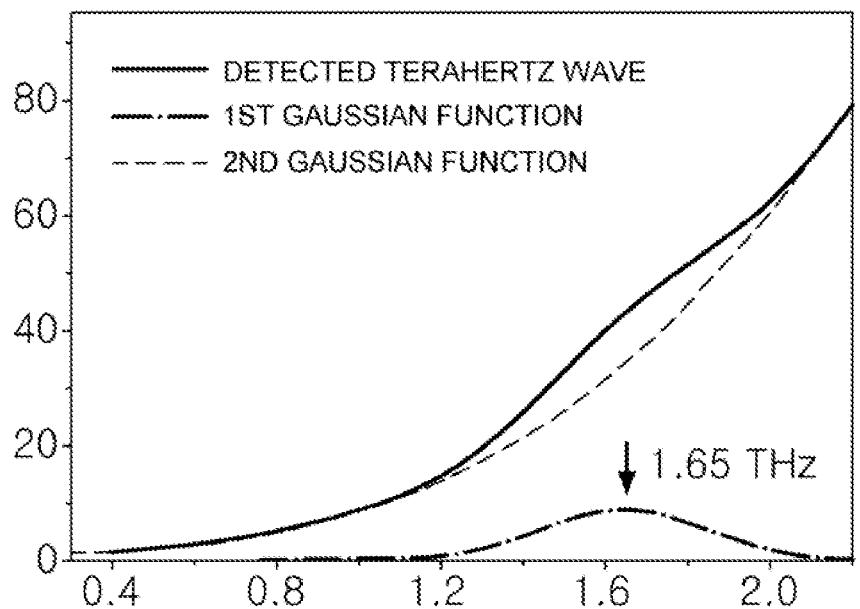
Figure 5C:
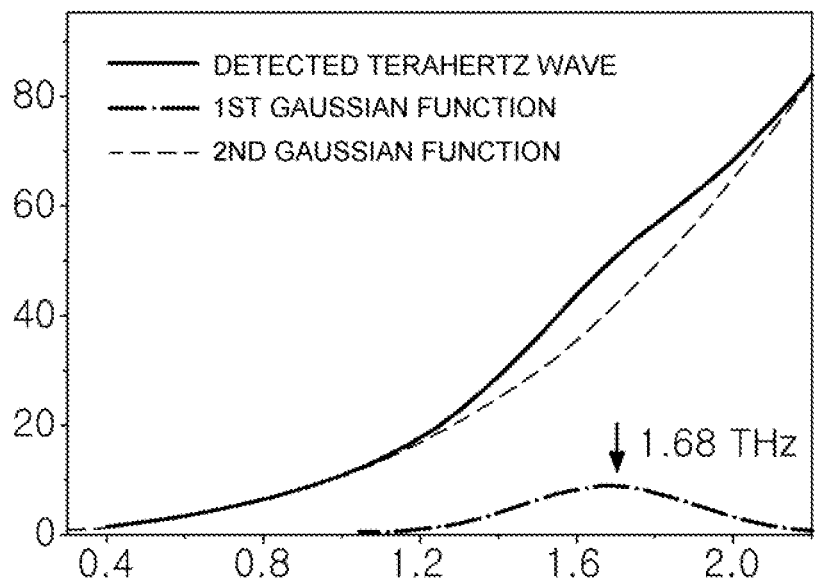
Figure 5D:
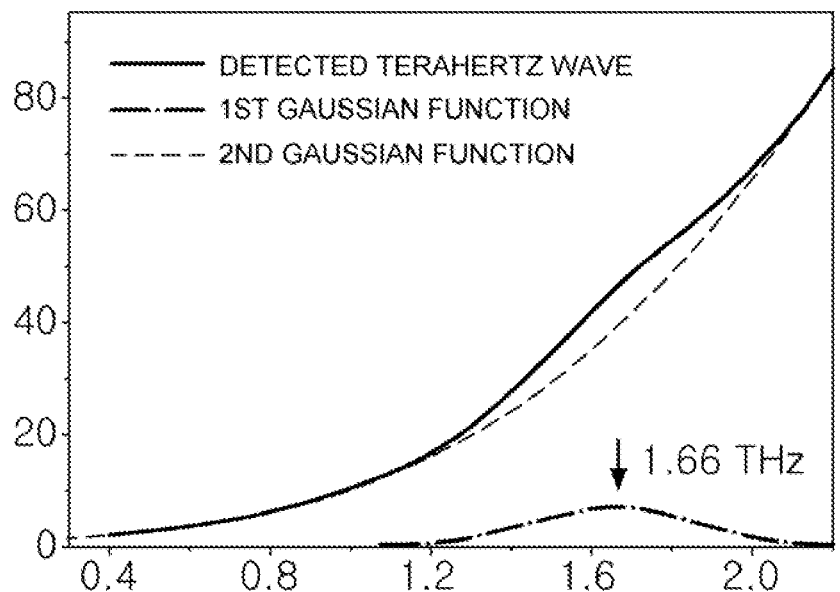

FIGS. 5A through 5D are graphs showing waveforms of the detected terahertz wave according to the present invention, wherein FIG. 5A illustrates a waveform of the detected terahertz wave when the sample DNA of the normal cell is irradiated with the terahertz wave, FIG. 5B illustrates a waveform of the detected terahertz wave when the sample DNA, which is obtained by methylating the DNA of the normal cell, is irradiated with the terahertz wave, FIG. 5C illustrates a waveform of the detected terahertz wave when the DNA of the prostate cancer cell is irradiated with the terahertz wave, and FIG. 5D illustrates a waveform of the detected terahertz wave when the DNA of the lung cancer cell is irradiated with the terahertz wave.

As shown in FIGS. 5A through 5D, the waveforms of the detected terahertz wave have a unique peak according to the type of cancer. Specifically, there is a peak at 1.68 THz for prostate cancer, and a peak at 1.66 THz for lung cancer.

Figure 6:
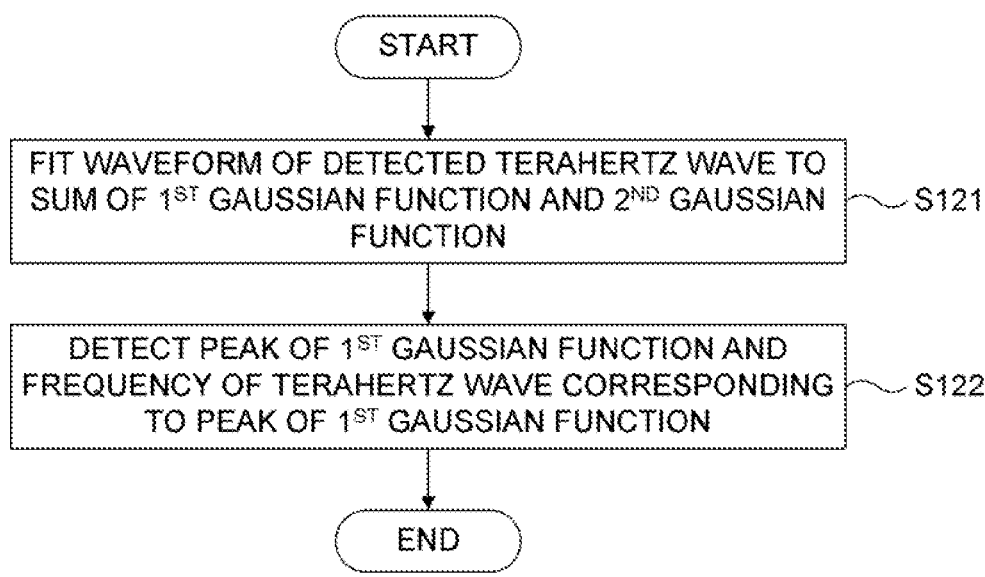
FIG. 6 is a flowchart illustrating in detail step S120 of FIG. 4.

FIG. 6 illustrates the method of detecting the peak in detail. Hereinafter, step S120 will be described in more detail with reference to FIG. 6.

FIG. 6 is a flow chart illustrating the step S120 of FIG. 4 in detail. Referring to FIG. 6, the waveform of the detected terahertz wave is fitted to the sum of a first gaussian function and a second gaussian function (S121). Specifically, the response signal (the detected terahertz wave indicated by solid lines in FIGS. 5A through 5D) obtained by irradiating the DNA with the terahertz wave while varying the frequency of the terahertz wave is curve-fitted to the first gaussian function and the second gaussian function as shown in FIGS. 5A through 5D. According to the findings of the inventors, this response signal is the sum of the first gaussian function (indicated by dash-dotted line) and the second gaussian function (indicated by dashed line). Therefore, the first gaussian function and the second gaussian function can be obtained from the response signal.

Thereafter, the peak of the first gaussian function and the frequency of the terahertz wave corresponding to the peak of the first gaussian function are detected (S122). Here, the frequency at the peak of the response signal corresponds to the frequency of the terahertz wave at the peak of the first gaussian function. Therefore, when the frequency of the terahertz wave at the peak of the first gaussian function is obtained, the frequency at the peak of the detected terahertz wave may be obtained.

Referring back to FIG. 4, the type of cancer is determined from the peak detected in step S120 (S130). Specifically, in step S130, the type of cancer is determined from the frequency of the terahertz wave corresponding to the peak of the first gaussian function detected in step S122. Since the frequency of the terahertz wave corresponding to the peak of the first gaussian function is unique for each type of cancer, the table of reference frequencies for different types of cancer may be stored in the memory, and the type of cancer can be determined by comparing the detected frequency and the reference frequencies to find a matching frequency.

Hereinafter, a DNA analyzing device in which the above-described DNA analysis method according to the present invention is performed will be described in detail with reference to FIG. 7.

Figure 7:
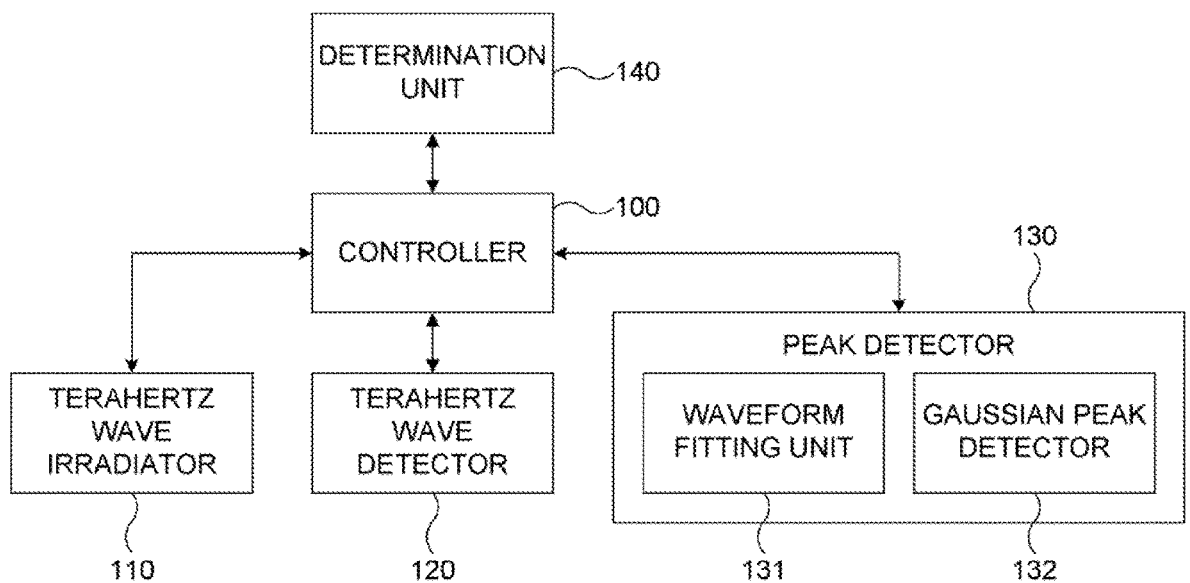
FIG. 7 is a block diagram illustrating a DNA analyzing device using terahertz wave according to the present invention.

FIG. 7 is a block diagram illustrating the DNA analyzing device using terahertz wave according to the present invention. Referring to FIG. 7, the DNA analyzing device according to the present invention includes a controller 100, a terahertz wave irradiator 110, a terahertz wave detector 120, a peak detector 130 and a determination unit 140.

The controller 100 controls the operation of the DNA analyzing device according to the present invention as well as the terahertz wave irradiator 110, the terahertz wave detector 120, the peak detector 130 and the determination unit 140.

The terahertz wave irradiator 110 irradiates terahertz wave onto methylated DNA. Preferably, the terahertz wave irradiator 110 irradiates the terahertz wave onto the methylated DNA while varying the frequency of the irradiated terahertz wave. That is, the terahertz wave irradiator 110 performs step S100 of FIG. 4.

The terahertz wave detector 120 detects a portion of the terahertz wave reflected by the methylated DNA. That is, the terahertz wave detector 120 performs step S110 of FIG. 4.

The peak detector 130 detects the peak of the waveform of the terahertz wave detected by the terahertz wave detector 120. That is, the peak detector 130 performs step S120 of FIG. 4.

The peak detector 130 may include a waveform fitting unit 131 and a gaussian peak detector 132.

The waveform fitting unit 131 fits the waveform to the sum of the first gaussian function and the second gaussian function. That is, the waveform fitting unit 131 performs step S121 of FIG. 6.

The gaussian peak detector 132 detects the peak of the first gaussian function and the frequency of the terahertz wave corresponding to the peak of the first gaussian function. That is, the gaussian peak detector 132 performs step S122 of FIG. 6.

The determination unit 140 determines the type of cancer from the peak detected by the peak detector 130. That is, the determination unit 140 performs step S130 of FIG. 4. Specifically, the determination unit 140 determines the type of cancer from the frequency of the terahertz wave corresponding to the peak of the first gaussian function detected by the gaussian peak detector 132.

Figure 8:
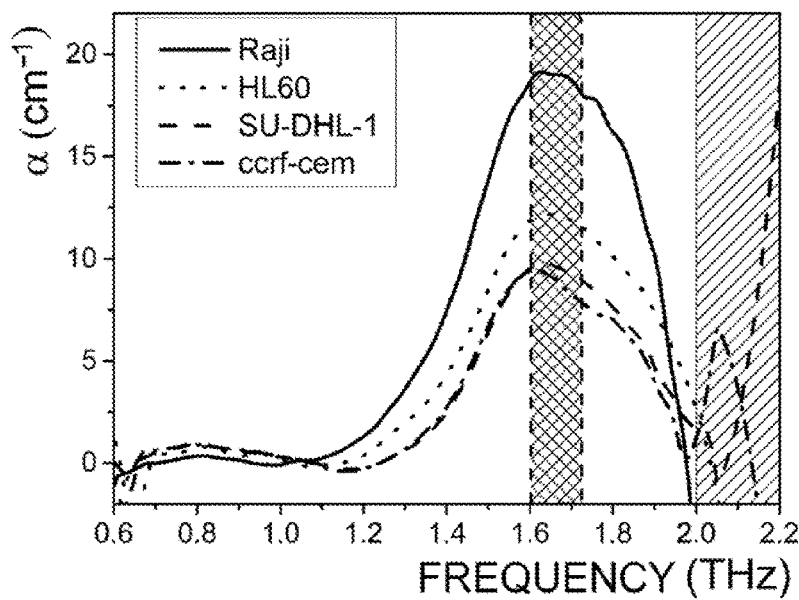
FIG. 8 is a graph showing the absorption coefficient for an actual leukemia carcinoma in a terahertz domain in a DNA analysis method using terahertz wave according to the present invention.

FIG. 8 is a graph showing the absorption coefficient for leukemic carcinoma in the terahertz domain in the DNA analysis method using the terahertz wave according to the present invention. FIG. 8 illustrates the terahertz absorption coefficient α of the DNA samples extracted from different leukemia carcinomas.

In FIG. 8, "Raji" refers to Burkitt's lymphoma, "HL-60" refers to acute promyelocytic leukemia, "SU-DHL-1" refers to Anaplastic Large Cell Lymphoblastic Leukemia (ALCL), and CCRF-CEM refers to acute lymphoblastic leukemia.

As shown in FIG. 8, the terahertz absorption coefficients α of the DNA samples have different peaks depending on the leukemia carcinomas. Therefore, the type of cancer may be accurately determined by using the DNA analysis method using the terahertz wave according to the present invention.

INDUSTRIAL APPLICABILITY

The DNA analysis method and DNA analyzing device of the present invention has industrial applicability since the type of cancer may be accurately determined from DNA using terahertz wave.

What is claimed is:

1. A DNA analysis method, comprising:
   (a) irradiating terahertz wave onto methylated DNA;
   (b) detecting the terahertz wave reflected from the methylated DNA;
   (c) detecting a peak of a waveform of the terahertz wave detected in the step (b); and
   (d) determining type of cancer from the peak detected in the step (c);
   wherein the step (c) comprises: (c-1) fitting the waveform into a sum of a first gaussian function and a second gaussian function; and (c-2) detecting a peak of the first gaussian function and a frequency of the terahertz wave corresponding to the peak of the first gaussian function.

2. The DNA analysis method of claim 1, wherein the step (d) comprises: determining the type of cancer from the frequency of the terahertz wave corresponding to the peak of the first gaussian function detected in the step (c-2).

3. The DNA analysis method of claim 2, wherein the step (a) comprises: irradiating the terahertz wave onto methylated DNA while varying a frequency of the terahertz wave.

4. A DNA analyzing device, comprising:
   a terahertz wave irradiator irradiating terahertz wave onto methylated DNA;
   a terahertz wave detector detecting the terahertz wave reflected from the methylated DNA;
   a peak detector detecting a peak of a waveform of the terahertz wave detected by the terahertz wave detector; and
   a determination unit determining a type of cancer from the peak detected by the peak detector;
   wherein the peak detector comprises: a waveform fitting unit fitting the waveform into a sum of a first gaussian function and a second gaussian function; and a gaussian peak detector detecting a peak of the first gaussian function and a frequency of the terahertz wave corresponding to the peak of the first gaussian function.

5. The DNA analyzing device of claim 4, wherein the determination unit determining the type of cancer from the frequency of the terahertz wave corresponding to the peak of the first gaussian function detected by the gaussian peak detector.

6. The DNA analyzing device of claim 5, wherein the terahertz wave irradiator irradiates the terahertz wave onto methylated DNA while varying a frequency of the terahertz wave.

* * * * *